United States Patent
Beachner et al.

(10) Patent No.: US 9,266,105 B2
(45) Date of Patent: Feb. 23, 2016

(54) SYSTEM AND METHOD FOR FORMING BONDED SUBSTRATES

(71) Applicant: Xerox Corporation, Norwalk, CT (US)

(72) Inventors: James R. Beachner, Ontario, NY (US); Jing Zhou, Pittsford, NY (US); Mandakini Kanungo, Penfield, NY (US); Nancy Y. Jia, Webster, NY (US); Paul J. McConville, Webster, NY (US); Wei Hong, Amherst, MA (US)

(73) Assignee: Xerox Corporation, Norwalk, CT (US)

( * ) Notice: Subject to any disclaimer, the term of this patent is extended or adjusted under 35 U.S.C. 154(b) by 74 days.

(21) Appl. No.: 14/311,970

(22) Filed: Jun. 23, 2014

(65) Prior Publication Data

US 2015/0367340 A1 Dec. 24, 2015

(51) Int. Cl.
*G01N 21/75* (2006.01)
*B01L 3/00* (2006.01)
*B32B 41/00* (2006.01)

(52) U.S. Cl.
CPC ............. *B01L 3/5023* (2013.01); *B32B 41/00* (2013.01); *B01L 2300/126* (2013.01); *B01L 2300/161* (2013.01); *B32B 2307/73* (2013.01); *B32B 2317/12* (2013.01); *Y10T 156/1741* (2015.01)

(58) Field of Classification Search
CPC ............ B01L 3/5023; B01L 2300/126; B01L 2300/161; Y10T 156/1741; B32B 41/00; B32B 2307/73; B32B 2317/12
See application file for complete search history.

(56) References Cited

U.S. PATENT DOCUMENTS

| 4,606,264 | A | | 8/1986 | Agronin et al. |
| 5,614,933 | A | * | 3/1997 | Hindman ................. B41J 2/005 347/103 |
| 5,820,284 | A | * | 10/1998 | Owada .............. B41M 5/38221 400/662 |
| 6,723,500 | B2 | * | 4/2004 | Yu ........................ G01N 33/558 422/401 |
| 7,267,938 | B2 | | 9/2007 | Anderson et al. |
| 8,377,710 | B2 | | 2/2013 | Whitesides et al. |
| 8,574,924 | B2 | | 11/2013 | Sia et al. |
| 8,603,832 | B2 | | 12/2013 | Whitesides et al. |
| 2002/0098124 | A1 | * | 7/2002 | Bentsen ............ B01L 3/502707 422/502 |
| 2004/0086424 | A1 | * | 5/2004 | Schembri .......... B01L 3/502707 422/504 |

(Continued)

OTHER PUBLICATIONS

Bracher et al.; Patterned paper as a template for the delivery of reactants in the fabrication of planar materials; The Royal Society of Chemistry Journal; Jun. 10, 2010; pp. 4303-4309.

(Continued)

*Primary Examiner* — Dennis M White
(74) *Attorney, Agent, or Firm* — Maginot Moore & Beck LLP

(57) ABSTRACT

An apparatus for bonding two substrates includes a first roller, a second roller that forms a nip with the first roller, a substrate transport configured to move the first substrate and a second substrate through the nip simultaneously, and a controller. The controller operates the substrate transport to move the first substrate and the second substrate through the nip simultaneously, with a pattern of a hydrophobic material on a first side of the first substrate engaging a first side of the second substrate. The first substrate engages the first roller, which has a higher temperature than the second roller, and the hydrophobic material penetrates the first and second substrates to bond the substrates together.

15 Claims, 6 Drawing Sheets

(56) References Cited

U.S. PATENT DOCUMENTS

| | | |
|---|---|---|
| 2010/0145491 A1 | 6/2010 | Troian |
| 2011/0111517 A1 | 5/2011 | Siegel et al. |
| 2011/0123398 A1 | 5/2011 | Carrilho et al. |
| 2012/0198684 A1 | 8/2012 | Carrilho et al. |
| 2012/0328905 A1 | 12/2012 | Guo et al. |
| 2013/0034869 A1 | 2/2013 | Whitesides et al. |

OTHER PUBLICATIONS

Martinez et al.; Diagnostics for the Developing World: Microfluidic Paper-Based Analytical Devices; Analytical Chemistry; Jan. 1, 2010; pp. 3-10; vol. 82, Issue No. 1; American Chemical Society.

* cited by examiner

100

SYSTEM AND METHOD FOR FORMING BONDED SUBSTRATES

TECHNICAL FIELD

This disclosure relates generally to systems and methods for bonding substrates together and, more particularly, to systems and methods for bonding layers of paper substrates to form a multilayer chemical assay or biomedical testing device.

BACKGROUND

Paper-based chemical assay devices include a paper substrate, wax that forms fluid channels and other fluid structures in the paper, and one or more reagents. Common examples of paper-based chemical assay devices include biomedical testing devices that are made of paper and perform biochemical assays and diagnostics in test fluids such as blood, urine and saliva. The devices are small, lightweight and low cost and have potential applications as diagnostic devices in healthcare, military and homeland security to mention a few.

Many of the paper-based diagnostic devices are formed from multiple layers of paper that is embedded with chemical reagents and with hydrophobic materials, such as wax or phase-change inks, that form channels to direct the diffusion of a biological fluid through the porous paper to one or more sites where the chemical reagents react with the biological fluid to perform the assay. When properly aligned, the multiple layers of paper enable three-dimensional paths for the fluid to reach the testing sites in the sensor, which enables a larger number of testing sites for different assays to be formed in a device of a given size compared to a two-dimensional arrangement in a single layer of paper. Additionally, some chemicals in the testing device are reactive to air or other environmental contaminants. The multiple layers of paper, with an optional coating of wax or another hydrophobic material, isolate portions of the testing device from the environment to prevent contamination.

Existing biomedical devices that are formed from multiple layers of paper or another substrate use adhesive layers that are interposed between the substrates to adhere multiple substrate layers together. For example, FIG. 6 depicts an exploded view of multiple paper layers 504A-504D that are bonded together with multiple corresponding layers of an adhesive film 508A-508C. Each layer of adhesive film is, for example, a two-sided adhesive tape. The adhesive film layers include holes, channels, and other perforations that enable liquid from one layer substrate layer to pass through the adhesive material to reach another layer of the substrate. For example, a fluid that is applied to the region 520 in the layer 504A passes through a corresponding opening 524 in the adhesive layer 508A to reach a corresponding fluid channel region 528 in the substrate layer 504B.

The separate adhesive layers that are used in the prior art biomedical have drawbacks during the manufacturing process and during use of biomedical sensors. During manufacture, the adhesive layers must be formed with openings that conform to the size, shape, and position of the openings in the two substrate layers that surround the adhesive. Forming the openings and aligning the substrate layers with the adhesive layer increases the complexity of the manufacturing process. During use, the biomedical sensor receives different biological fluids. In some instances, the biological fluids are chemically reactive with the adhesive material in the adhesive layers. The reactions between the fluid and the adhesive may contaminate the biomedical sensor and reduce the accuracy of assay results. Consequently, improvements to the production process and structure of multi-layer biomedical sensors and other multi-layer devices would be beneficial.

SUMMARY

In one embodiment, an apparatus that bonds a first substrate to a second substrate has been developed. The apparatus includes a first roller, a second roller configured to engage the first roller to form a nip, a first heater operatively connected to the first roller and configured to heat the first roller to a first temperature that is greater than a second temperature of the second roller, a substrate transport configured to move the first substrate and a second substrate through the nip simultaneously, and a controller operatively connected the first heater and the substrate transport. The controller is configured to activate the first heater to heat the first roller to the first temperature, and operate the substrate transport to move the first substrate and the second substrate through the nip with a predetermined pattern of a hydrophobic material on the first side of the first substrate engaging a first side of the second substrate, a second side of the first substrate engaging the second roller and a second side of the second substrate engaging the first roller to enable the hydrophobic material in the predetermined pattern to bond the first substrate to the second substrate.

In another embodiment, a method for bonding a first substrate to a second substrate has been developed. The method includes activating with a controller a first heater to heat a first roller to the first temperature, engaging with the controller a second roller to the first roller to form a nip, the second roller having a second temperature that is lower than the first temperature, and operating with the controller a substrate transport to move the first substrate and a second substrate through the nip with a predetermined printed pattern of a hydrophobic material on the first side of the first substrate engaging a first side of the second substrate, a second side of the first substrate engaging the second roller and a second side of the second substrate engaging the first roller to enable the hydrophobic material in the predetermined printed pattern to bond the first substrate to the second substrate.

In another embodiment, a multi-layer chemical assay device that is configured to direct a diffusion of a fluid has been developed. The sensor includes a first substrate comprising a first side with a predetermined location that is configured to receive a biological fluid sample, a second substrate with a first side that engages a second side of the first substrate to receive fluid from the biological fluid sample that diffuses through the first substrate, and a hydrophobic material that penetrates the first substrate and the second substrate to bond the first substrate to the second substrate.

BRIEF DESCRIPTION OF THE DRAWINGS

The foregoing aspects and other features of an apparatus that controls the bonding of substrates are explained in the following description, taken in connection with the accompanying drawings.

DETAILED DESCRIPTION

Figure 1:
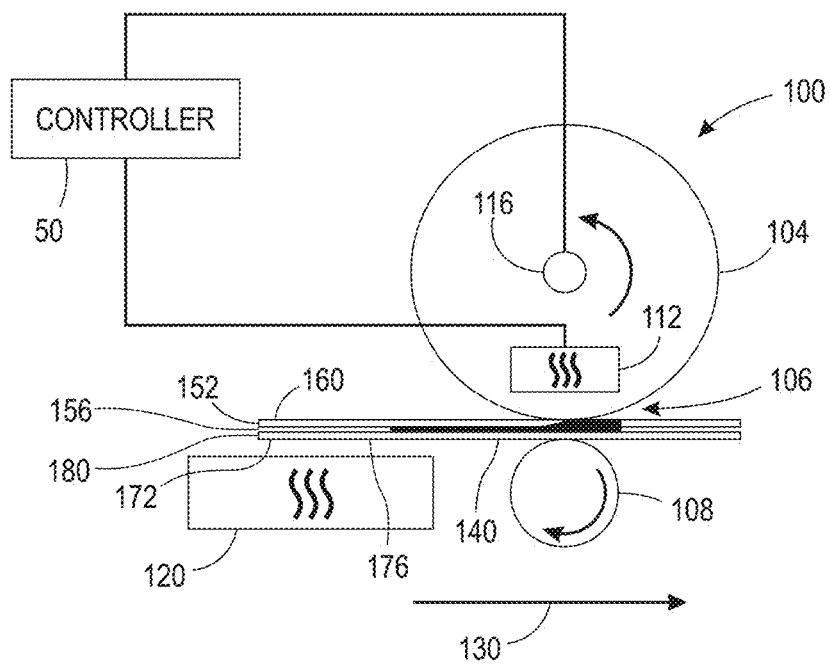
FIG. 1 is a diagram of an apparatus that is configured to bond two substrates together with hydrophobic material that is deposited on one of the substrates.

For a general understanding of the environment for the system and method disclosed herein as well as the details for the system and method, reference is made to the drawings. In the drawings, like reference numerals have been used throughout to designate like elements. As used herein, the word "printer" encompasses any apparatus that produces images with colorants on media, such as digital copiers, bookmaking machines, facsimile machines, multi-function machines, or the like. In the description below, a printer is further configured to deposit a melted wax, phase-change ink, or other hydrophobic material onto a porous substrate, such as paper. The printer is optionally configured to apply a temperature gradient and pressure to the substrate that spreads the hydrophobic material and enables the hydrophobic material to penetrate into the porous substrate to form channels and barriers that control the capillary flow of liquids, including water, through the substrate.

As used herein, the terms "hydrophilic material" and "hydrophilic substrate" refer to materials that absorb water and enable diffusion of the water through the material via capillary action. One common example of a hydrophilic substrate is paper, such as cellulose filter paper, chromatography paper, or any other suitable type of paper. The hydrophilic substrates are formed from porous materials that enable water and other biological fluids that include water, such as blood, urine, saliva, and other biological fluids, to diffuse into the substrate. As described below, a hydrophobic material is embedded in the hydrophilic substrate to form channels and other structures that control the diffusion of the fluid through the hydrophilic substrate.

As used herein, the term "hydrophobic material" refers to any material that resists adhesion to water and is substantially impermeable to a flow of water through capillary motion. When embedded in a porous substrate, such as paper, the hydrophobic material acts as a barrier to prevent the diffusion of water through portions of the substrate that include the hydrophobic material. The hydrophobic material also acts as a barrier to many fluids that include water, such as blood, urine, saliva, and other biological fluids. As described below, the hydrophobic material is embedded in a porous substrate to form hydrophobic structures that include, but are not limited to, fluid barriers, fluid channel walls, and other elements that control the capillary diffusion of the liquid through the substrate. In one embodiment, the substrate also includes biochemical reagents that are used to test various properties of a fluid sample. The hydrophobic material forms channels to direct the fluid to different locations in the substrate that have deposits of the chemical reagents. The hydrophobic material is also substantially chemically inert with respect to the fluids in the channel to reduce or eliminate chemical reactions between the hydrophobic material and the fluids. A single sample of the fluid diffuses through the channels in the substrate to react with different reagents in different locations of the substrate to provide a simple and low-cost device for performing multiple biochemical tests on a single fluid sample.

As used herein, the term "phase-change material" refers to a form of hydrophobic material with a solid phase at room temperature and standard atmospheric pressure (e.g. 20° C. and one atmosphere of pressure) and a liquid phase at an elevated temperature and/or pressure level. Examples of phase-change materials used herein include wax and phase-change ink. As used herein, the term "phase-change ink" refers to a type of hydrophobic phase-change material in the form of an ink that is substantially solid at room temperature but softens and liquefies at elevated temperatures. Some inkjet printers eject liquefied drops of phase-change ink onto indirect image receiving surfaces, such as a rotating drum or endless belt, to form a latent ink image. The latent ink image is transferred to a substrate, such as a paper sheet. Other inkjet printers eject the ink drops directly onto a print medium, such as a paper sheet or an elongated roll of paper. In a liquid state, the phase-change material can penetrate a porous substrate, such as paper. Examples of phase-change inks that are suitable for use in forming fluid channels and other hydrophobic structures in hydrophilic substrates include solid inks that are sold commercially by the Xerox Corporation of Norwalk, Conn.

As described below, two substrates pass through a nip between two rollers that apply a temperature gradient and pressure to the phase-change hydrophobic material. The phase-change material transitions to the liquid phase and penetrates both substrates. The phase-change material subsequently cools and solidifies to bond the two substrates together. The embodiments of phase-change materials that are described herein for use with biological sensors are also hydrophobic materials that present a barrier to the diffusion of water and other biological fluids through the substrate. The phase-change materials are also substantially chemically non-reactive to the biological fluids in the biological sensor embodiments. In alternative embodiments, however, a phase-change material that bonds two substrates together is not necessarily a hydrophobic material.

As used herein, the term "dwell time" refers to an amount of time that a given portion of two or more substrates spend in a nip that is formed between two rollers to receive heat and pressure that binds the substrates together. The amount of dwell time is related to the surface areas of the rollers that form the nip and the linear velocity of the substrate through the nip. The dwell time is selected to enable the phase-change material to penetrate the substrates to bind the substrates together. The selected dwell time can vary based on the thickness and porosity of the substrates, the temperature gradient in the nip, the pressure in the nip, and the viscosity characteristics of the phase-change material that binds the substrates together. Larger rollers typically form a nip with a larger surface area. Thus, embodiments of bonding apparatuses with larger roller diameters operate with a higher linear velocity to achieve the same dwell time as other embodiments with smaller diameter rollers.

In a traditional inkjet printer, the phase-change ink is transferred to one side of a substrate, with an option to transfer different phase-change ink images to two sides of a substrate in a duplex printing operation. The printer spreads the phase-change ink drops on the surface of the substrate, and the phase-change ink image cools and solidifies on the surface of the print medium to form a printed image. The embodiments described below, however, apply heat and pressure to phase-change ink or another phase-change hydrophobic material on the surface of the substrate to enable the phase-change material to penetrate through the porous material in the substrate to form a three-dimensional barrier through the thickness of the substrate that controls the diffusion of fluids through the substrate.

FIG. 1 depicts an apparatus 100 for applying heat and pressure to two substrates, such two sheets of paper, to enable a hydrophobic material that is formed on one of the substrates to flow into the porous material of both substrates and bond the substrates together. In some embodiments, the apparatus 100 is incorporated in an inkjet printing system.

In FIG. 1, the apparatus 100 includes a first roller 104, second roller 108, roller heater 112, rotating actuator 116, substrate heater 120, and controller 50. The first roller 104 and second roller 108 engage each other in a nip 106. In the apparatus 100, mechanical, pneumatic, or hydraulic actuators hold the rollers 104 and 108 together to form the nip 106 with varying levels of pressure to apply pressure to one or more substrates that pass through the nip 106. In some embodiments, the actuators also move the rollers 104 and 108 into engagement to form the nip 106 or out of engagement. The rotating actuator 116 is, for example, an electric motor that rotates the first roller 104 at a range of selected velocities. The second roller 108 rotates in response to the motion of the first roller 104 when engaged to the first roller 104.

In the apparatus 100, a substrate transport propels a substrate in a direction indicated by the arrow 130 to pass through the nip 106. The substrate transport includes one or more actuators and belts, rollers, and other transport devices that move the substrate through the nip in synchronization with the motion of the rollers 104 and 108. The first roller 104 and second roller 108 are part of the substrate transport system that propels the substrate through the nip 106. In an embodiment where the apparatus 100 is incorporated in an inkjet printer, the substrate transport system in the printer transports the substrate. Some inkjet printers include a duplex substrate transport that moves a substrate through the nip 106 to receive the hydrophobic material on one side of the substrate from the first roller 104, and returns the substrate through the nip 106 with the side that received the hydrophobic material engaging the second roller 108.

The apparatus 100 includes the roller heater 112 that heats the surface of the roller 104 to a range of elevated temperatures. As described below, the heater 112 heats the roller 104 to different surface temperatures of the roller 104 to enable the hydrophobic material to penetrate the substrate and for transferring latent images formed from the hydrophobic material onto a surface of a substrate in the optional inkjet printer embodiment. The substrate heater 120 is another heater that is positioned along the path of the substrate through the substrate transport prior to the nip 106. The substrate heater 120 elevates the temperature of the substrate to a predetermined temperature as the substrate passes through the nip 106. In one embodiment, the substrate heater 120 heats the substrate to 60° C. as the substrate approaches the nip 106. The roller heater 112 and substrate heater 120 are embodied as electric radiant heaters in the apparatus 100.

In the apparatus 100, the controller 50 is, for example, a self-contained, dedicated digital computing device including having a central processor unit (CPU) and a digital memory. The controller 50 is operatively connected to the actuator 116 and heater 112, among other components in the apparatus 100. During operation, the controller 50 receives digital image data corresponding to patterns of the hydrophobic material that are formed on sides of one or more substrates. The hydrophobic material forms barriers and fluid channels that control the diffusion of fluid samples through hydrophilic substrates such as paper. Additionally, regions of the hydrophobic material coat the sides of the substrate to seal the substrate or other substrate layers in a stacked multi-layer device from contamination.

The controller 50 is be implemented with general or specialized programmable processors that execute programmed instructions to control the operation of one or more components in the apparatus 100. The instructions and data required to perform the programmed functions are stored in the memory that is associated with the processors or controllers. These components in the controller 50 are provided on a printed circuit card or provided as a circuit in an application specific integrated circuit (ASIC). Each of the circuits can be implemented with a separate processor or multiple circuits are implemented on the same processor. In alternative configurations, the circuits are implemented with discrete components or circuits provided in very large scale integration (VLSI) circuits. Also, the circuits described herein can be implemented with a combination of processors, FPGAs, ASICs, or discrete components.

Figure 3A:
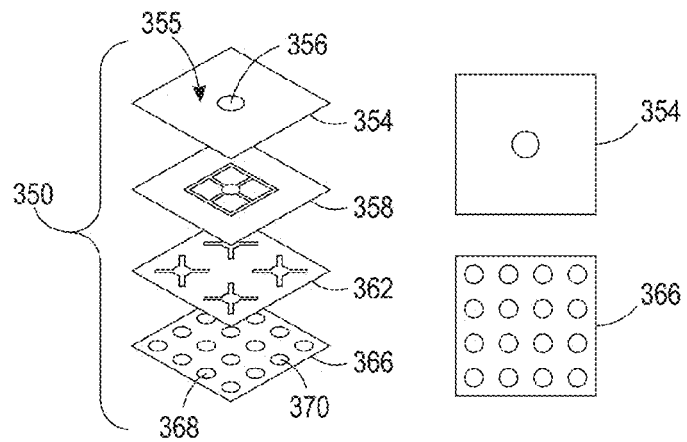
FIG. 3A is an exploded view of a multi-layer biomedical testing device that includes a plurality of substrates bonded together by a hydrophobic material that is formed on the surface of the substrates.

FIG. 3A depicts an example of printed hydrophobic layers that are formed on different substrate layers in a multi-layer chemical assay device. In the embodiment of FIG. 3A, the chemical assay device is embodied as a biomedical test device 350 that includes a deposit location and fluid channels formed from the hydrophobic material to direct the fluid to different locations where chemical reagents react with the fluid. The device 350 includes four substrate layers 354, 358, 362, and 366. The layer 354 is an inlet layer with a region 355 that the apparatus 100 forms from the hydrophobic material and a deposit site 356 that is formed from the bare paper substrate and receives drops of a biomedical fluid. The hydrophobic material in the region 355 seals the biomedical device 350 from one side and controls the diffusion of biomedical fluids that are placed on the deposit site 356. The apparatus 100 deposits different printed arrangements of the hydrophobic material onto the layers 358, 362, and 366 as depicted in FIG. 3. The layers 358 and 362 form intermediate fluid channels that direct the fluid from the layer 352 to different test sites in the layer 366. For example, the test site 368 includes a chemical reagent that tests for protein levels in a blood sample and the test site 370 includes a chemical reagent that tests for glucose levels in the blood sample. The printed arrangement on the substrate layer 366 forms barriers to prevent diffusion of the fluid between the test sites and enables the substrate layer 366 to be bonded to the substrate layer 364.

Referring to FIG. 1 the apparatus 100 is depicted in an operating mode where the substrate 152 that already bears hydrophobic material 140 on one side 156 passes through the nip 106 with another substrate 172 where pressure and a temperature gradient are applied to both the substrates 152 and 172 to enable the hydrophobic material 140 to liquefy in the nip 106 and bond the substrates 152 and 172 together. The substrates 152 and 172 move through the nip 106 with the side 160 of the substrate 152 engaging the roller 104, the side 156 bearing the printed pattern 140 engaging one side 180 of the substrate 172, and another side 176 of the substrate 172 engaging the second roller 108. In the embodiment of FIG. 1, the substrate transport aligns both of the substrates 152 and 172 along the edges of the substrate sheets, such as aligning two sheets of paper along common edges. An inkjet printing system (not shown) or another suitable device form the patterns with sufficient precision to align corresponding fluid channels and printed regions of the hydrophobic material between two media sheets when the media sheets are aligned at the edges and passed through the nip 106.

In FIG. 1, the roller heater 112 heats the surface of the first roller 104 to a temperature of approximately 100° C. The surface of the second roller 108 remains at a lower temperature of approximately 20° C.-40° C. To maintain the lower temperature during operation, an actuator (not show) removes the second roller 108 from the nip 106 during periods of operation when a substrate is not moving through the nip 106. While the second roller 108 receives some thermal energy from the first roller 104, the separation of the second roller 108 from the first roller 104 enables the second roller 108 to remain at a lower temperature than the first roller 104 to form a temperature gradient when a substrate passes through the nip 106. In other embodiments that use a hydrophobic phase-change ink as material to bond the substrates, the surface of the first roller is heated to an elevated temperature in a range of 65° C. to 140° C., although other temperatures ranges may be suitable for different hydrophobic material compositions.

In the apparatus 100, the surface temperature of the second roller remains lower than the surface temperature of the first roller for any selected temperature in the range. The different surface temperatures in between the rollers 104 and 108 form a temperature gradient in the nip 106 as the substrates 152 and 172 move through the nip 106. The side 160 of the substrate 152 is heated to a higher temperature than the side 176 of the substrate 172 in the nip 106. The temperature gradient formed in the nip 106 enables the hydrophobic material 140 penetrates into the substrate 152 toward the higher temperature roller 104 to a greater degree than the penetration of the hydrophobic material 140 into the substrate 172. The hydrophobic material 140 penetrates both substrates to a sufficient degree to bond the substrates 152 and 172 together. The first roller 104 and second roller 108 also apply pressure to the substrate 152 and hydrophobic material 140 with a nip pressure that is selected in a range of between 800 pounds per square inch (PSI) and 3,000 PSI in the embodiment of FIG. 1.

During operation, the actuator 116 rotates the first roller 104 at a predetermined linear velocity of to move the substrate 152 through the nip 106 at rate that provides sufficient dwell time for the hydrophobic material 140 to penetrate the substrates 152 and 172. The linear velocity is selected to enable each portion of the substrates 152 and 172 to remain within the nip 106 for a predetermined dwell time of between 0.1 second and 10 seconds. As described above, the size and surface areas of the rollers 104 and 108 affect the size of the nip and the controller 50 operates the actuator 116 to adjust the linear velocity of the first roller 104 and second roller 108 to produce a predetermined dwell time that is selected based on the types of substrates and hydrophobic material that binds the substrates.

Figure 2:
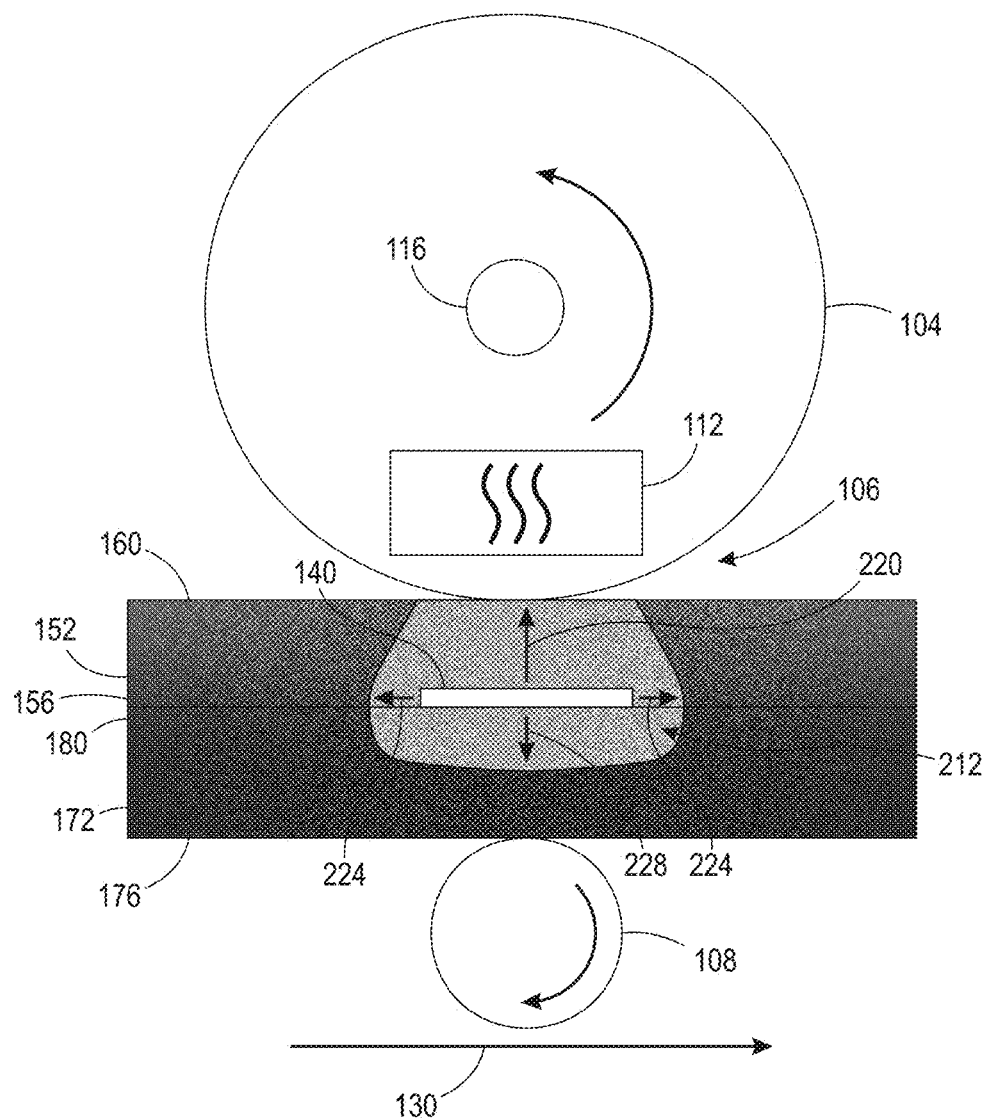
FIG. 2 is a diagram depicting the flow of a hydrophobic material in a liquid phase as two substrates are bonded together in a nip of the apparatus of FIG. 1.

FIG. 2 depicts the penetration of the hydrophobic material 140 into the substrates 152 and 172 in more detail. The elevated temperature and pressure in the nip 106 melt the solidified hydrophobic material 140 and the liquefied hydrophobic material spreads both horizontally and vertically into the porous material in the substrates 152 and 172 as depicted by the region 212 that extends into the porous material of both the substrates 152 and 172. The spreading distance L of the liquefied hydrophobic material is provided by Washburn's equation:

$$L = \sqrt{\frac{\gamma D t}{4\eta}}$$

where $\gamma$ is the surface tension of the melted hydrophobic material 140, D is the pore diameter of pores in the substrates 152 and 172, t is the amount of time that the hydrophobic material 140 remains liquefied, and $\eta$ is the viscosity of the melted hydrophobic liquid. The surface tension $\gamma$ and viscosity $\eta$ terms are empirically determined from the properties of the hydrophobic material 140. The pore diameter D is empirically determined from the type of paper or other hydrophilic material that forms the substrates 152 and 172. While not a requirement, the substrates 152 and 172 have the same pore diameters D in the embodiment of FIG. 2.

As set forth above in Washburn's equation, the spreading distance L is inversely related to the viscosity $\eta$ of the hydrophobic liquid. The apparatus 100 has direct or indirect control over viscosity $\eta$ of the hydrophobic material as the hydrophobic material and substrate move through the temperature gradient that is produced in the nip 106 and the dwell time t. Hydrophobic materials such as wax or phase-change inks transition into a liquid state with varying levels of viscosity based on the temperature of the material and pressure applied to the hydrophobic material. The viscosity of the liquefied hydrophobic material is inversely related to the temperature of the material. The temperature gradient in the nip reduces the viscosity of the hydrophobic material in the higher-temperature region near the side 160 of the substrate 152 and roller 104 to a greater degree than on the cooler side 176 of the substrate 172 and cooler roller 108.

As is known in the art, the pressure applied in the nip 106 also reduces the effective melting temperature of the hydrophobic material 140 so that the temperature levels required to melt the hydrophobic material 140 in the nip 106 are lower than the melting temperature at standard atmospheric pressure. As the substrates 152 and 172 exit the nip, the pressure level drops rapidly, which enables the hydrophobic material 140 to return to a solidified state in a more rapid and controlled manner to bond the substrates 152 and 172. The linear velocity of the substrates 152 and 172 through the nip 106 also affects the amount of time that the hydrophobic material 140 spends in the liquid state.

In the nip 106, the temperature gradient produces anisotropic heating of the melted hydrophobic material 140. The higher temperature of the first roller 104 on the side 160 lowers the viscosity $\eta$ of the hydrophobic material 140 near the higher temperature first roller 104 to a greater degree than the viscosity of the hydrophobic material 140 near the lower temperature second roller 108. Thus, the temperature gradient enables the hydrophobic material 140 to flow into the porous material of the substrate 152 toward the side 160 for a longer distance than the flow of the hydrophobic material into the substrate 172 toward the side 176. In the region 212, the arrow 220 depicts a longer distance of flow for the hydrophobic material toward the higher temperature roller 104 compared to a comparatively shorter flow in direction 228 into the substrate 172 toward the lower temperature roller 108. The temperature gradient also reduces the horizontal flow of the hydrophobic material 140 along the length of the substrates 152 and 172 as indicated by the arrows 224. The temperature gradient in the nip 106 enables the hydrophobic material 140 to transition to the liquid phase and penetrate into both substrates 152 and 172 to bond the substrates together. In the example of FIG. 2, the hydrophobic material 140 penetrates through from the side 152 to the side 160. The penetration of the hydrophobic material enables the hydrophobic material to form barriers and fluid channels through the substrate 156. The reduced penetration into the substrate 172 prevents the hydrophobic material 140 from blocking or otherwise interfering with fluid channels that are formed from additional layers of the hydrophobic material in the second substrate 172, but a sufficient portion of the hydrophobic material 140 penetrates the second substrate 172 to form a secure bond between the substrates 152 and 172.

Figure 3B:
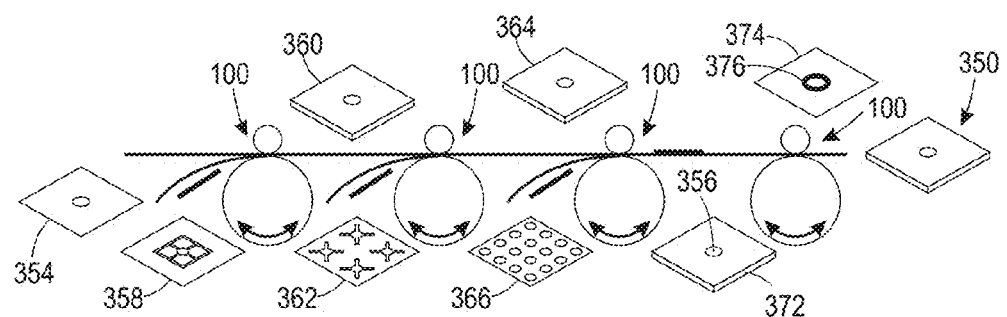
FIG. 3B is a diagram depicting the formation of a multi-layer biomedical testing device from multiple individual paper substrates that are coated with a hydrophobic material to bond the substrates together and to form channels that control the diffusion of fluid through the paper substrates.

FIG. 3B depicts a process of bonding multiple substrate layers of the device 350 together using the apparatus 100. In FIG. 3B, the apparatus 100 passes the substrates 354 and 358 pass through the nip to bond the layers together as depicted by the bonded layers 360. The apparatus 100 subsequently moves the bonded layers 360 through the nip with the next layer 362 to form three bonded layers 364, and the apparatus continues in a similar manner to bond the substrate 366 to the three bonded layer 364, which forms the device 350. FIG. 3B depicts a single apparatus 100 that bonds together successive substrate layers to form the device 350. Another embodiment uses multiple sets of rollers that are similar to the apparatus 100 to bond multiple substrate layers together.

In FIG. 3B, at least some of the substrate layers include a hydrophobic material for forms fluid channels through the substrates in addition to hydrophobic material that bonds the multiple substrate layers together. For example, the substrate layer 358 includes fluid channels 359 that are formed in through the thickness of the substrate. During the initial bonding process in the apparatus 100 between the substrates 354 and 358, the higher-temperature first roller 104 engages the substrate 358. The anisotropic temperature gradient in the nip 106 enables the hydrophobic material on the substrate 358 to penetrate into the substrate 358 to form the fluid channels. Additionally, a portion of the hydrophobic material penetrates both substrates 354 and 358 to bond the substrates together. During subsequent bonding operations for the substrate layers 362 and 366, the previously bonded stack of layers engages the lower-temperature second roller 108 while the additional layer engages the higher-temperature roller 104 in the apparatus 100. The fluid channels that are formed in the previously bonded substrates are not substantially affected by subsequent passes through the apparatus 100 that bond additional layers to form the device 350.

Figure 4:
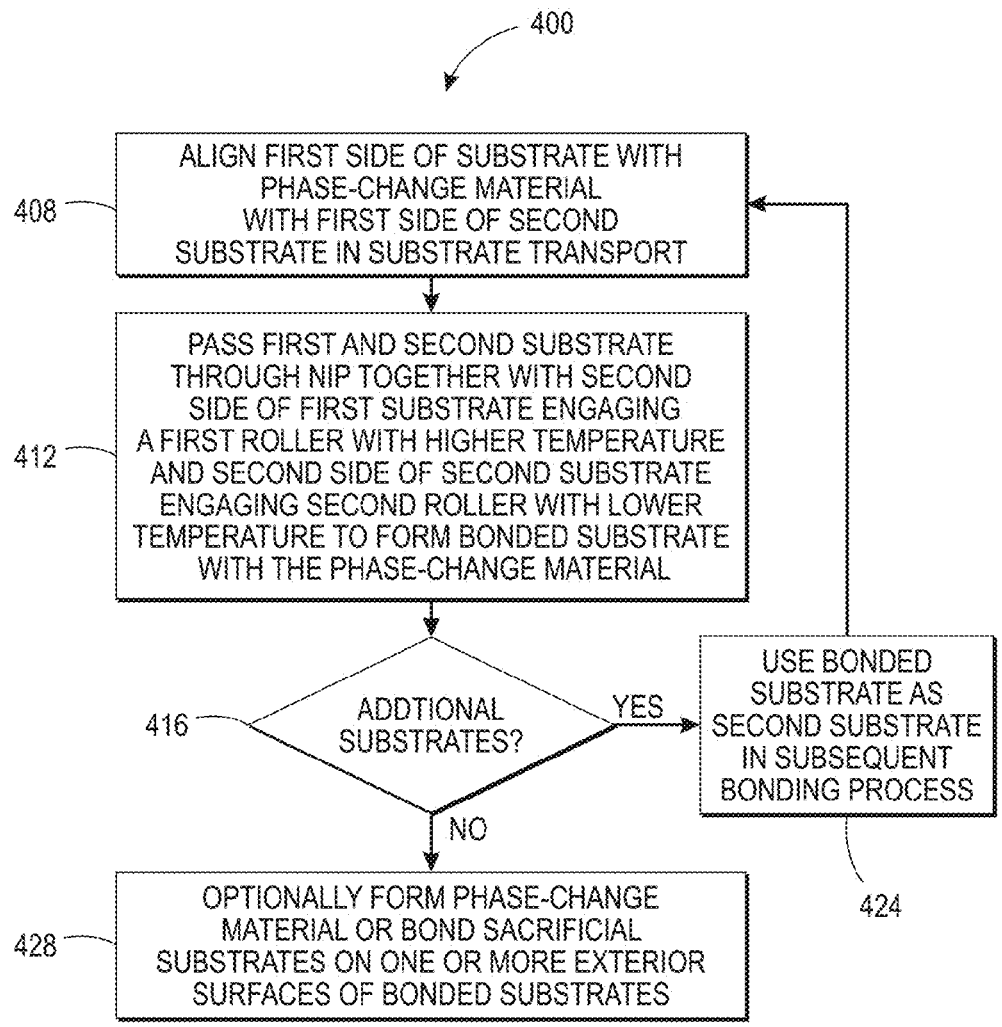
FIG. 4 is a block diagram of a process for bonding multiple substrates together using a hydrophobic material.

FIG. 4 depicts a block diagram of a process 400 for bonding two or more substrates together using a hydrophobic material. The process 400 is described in conjunction with the apparatus 100 of FIG. 1 and FIG. 2, and the biomedical testing device 350 of FIG. 3A and FIG. 3B for illustrative purposes.

The process 400 begins as the apparatus 100 as the substrate transport aligns the printed substrate with a first side of a second substrate (block 408). In the apparatus 100, the two substrates are aligned along at least two perpendicular edges using substrate handling devices that are used in existing printer devices. The alignment of the substrates along the edges ensures that the printed patterns of the hydrophobic material in different substrate layers are also aligned with each other to form fluid channels that are connected together through multiple substrate layers.

Process 400 continues as the apparatus 100 passes the two substrates through the nip 106 with a second side of the first substrate engaging the first roller with the higher temperature and a second side of the second substrate engaging the second roller with the lower temperature (block 412). The hydrophobic material liquefies in the nip and bonds the two substrates together. FIG. 1 and FIG. 2 depict the bonding process in more detail. As described above, the temperature gradient in the nip from the higher temperature of the first roller to the lower temperature of the second roller enables the liquefied hydrophobic material to penetrate the first substrate to a greater degree than the second substrate.

Process 400 continues for any additional substrates that are used to form the device (block 416). During process 400, the previously bonded substrates are passed through the nip as the second substrate that is described with reference to the processing of blocks 408 and 412 (block 424). The first substrate is an additional layer that is bonded to the previously bonded substrate layers. The apparatus 100 bonds an additional substrate layer during each iteration of the processing described with reference to blocks 408-424.

After all of the layers have been bonded together, apparatus 400 optionally prints an additional hydrophobic material pattern on the second of the last bonded substrate at the end of the bonding process (block 428). The additional layer of the hydrophobic material seals an exposed portion of the final substrate layer that is bonded to the remaining substrate layers. For example, in the sensor 350 if the layer 366 is the final layer that is bonded to the substrates in the sensor 350, then the apparatus 100 optionally prints a pattern of the phase-change ink that seals the exposed surface of the layer 366 on the bottom of the biomedical testing device 350. In the biomedical testing device 350, the test sites need to be visible to a user, but the test sites may become contaminated by fluids or air if the paper substrate is exposed. In one embodiment of the process 400, an inkjet printer or other device forms a coating of an optically transparent wax or phase-change ink that completely seals the exposed lower surface of the layer 366 while enabling the test sites, such as the test sites 368 and 370, to remain visible when the device 350 is used to analyze a fluid sample.

In another embodiment, the process 400 forms a seal on an exterior surface of a bonded substrate stack, such as the sensor 350, with a sacrificial substrate layer. The sacrificial substrate layer is coated with the hydrophobic material and bonded to the exterior of the sensor 350, such as the exposed surface of the substrate layer 366. The sacrificial substrate is peeled away from the biosensor 350 after being passed through the apparatus 100. The bonding apparatus 100 forms a weak bond between the sacrificial layer and the exposed layer of the biosensor 350 in which a majority of the hydrophobic material that is formed on the sacrificial layer is transferred to the exposed surface of the biosensor 350. The sacrificial layer is then peeled away either manually at the time of use of the biosensor 350, or in an automated manner.

FIG. 3 depicts a sacrificial substrate 374 that is bonded to the substrate 354 in the biosensor 350 around the deposit 356. The sacrificial substrate 374 includes a circular deposit of the hydrophobic material 376 that bonds the sacrificial substrate 374 to the substrate 354 without blocking the deposit site 356. The hydrophobic material 376 does not cover the full surface of the sacrificial substrate 374 to enable manual or automatic separation of the sacrificial substrate from the substrate layer 354 in the sensor 350. While not depicted in FIG. 3, another sacrificial layer is optionally bonded to the bottom substrate 366 in the sensor 350. The bottom sacrificial layer receives a pattern of the hydrophobic material that does not cover the reaction sites 368, 370 or any other reaction sites in the substrate layer 366. As described above, the hydrophobic material that is formed on the sacrificial layer is optionally an optically transparent wax or ink for the sensor 350 where the exposed surface of the substrate layer 366 that includes reaction sites 368 and 370 for biomedical analysis remain visible but are protected from contamination.

The biosensor and the sacrificial layer pass through the apparatus 100 with the sacrificial layer engaging the lower-temperature second roller 108 and the bonded substrate layers in the sensor 372 engaging the higher-temperature first roller 104. Thus, the temperature gradient in the nip of the apparatus 100 draws the phase-change ink toward the layer 354 in a similar manner to the substrate layer 152 in FIG. 2. The distribution of the hydrophobic material forms a comparatively weak bond between the substrate layer 354 and the sacrificial substrate 374 that enables manual or automated separation of the substrate 374 from the substrate layer 354 without damaging the surface of the substrate layer 354.

While FIG. 3 depicts a configuration where the sacrificial substrate layer engages the lower-temperature second roller instead of the higher-temperature first roller, in another configuration the sacrificial layer engages the higher-temperature first roller of the apparatus 100 to form a bond between the sacrificial substrate layer 374 and the other layers in the biomedical testing device 350. In this embodiment, the sacrificial substrate layer 374 is bonded to the other substrate layers in substantially the same manner as the other substrate layers in the biomedical testing device 350. As described below, the temperature of the first roller can affect the strength of the bond between two or more substrates. In another embodiment, the first roller in the apparatus 100 that bonds the sacrificial substrate layer 374 is optionally heated to a higher temperature to form a weaker bond between the sacrificial substrate layer 374 and the other substrate layers in the biomedical testing device 350.

Figure 5:
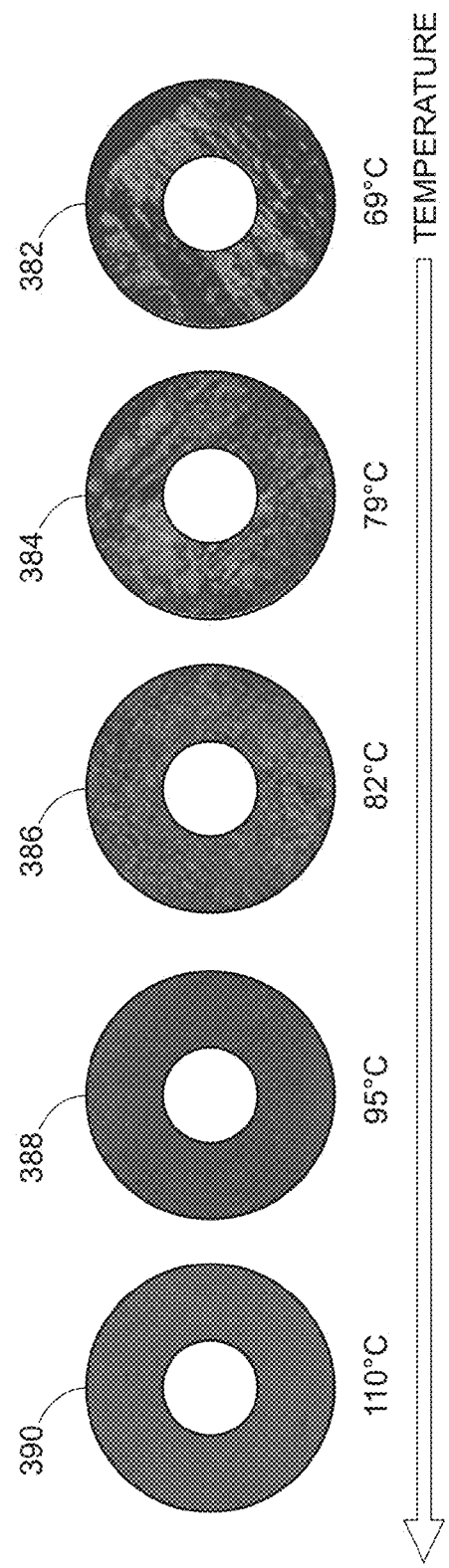
FIG. 5 is a diagram depicting the penetration of hydrophobic material to a first substrate after removal of another substrate that is bound to the first substrate.
Figure 6:
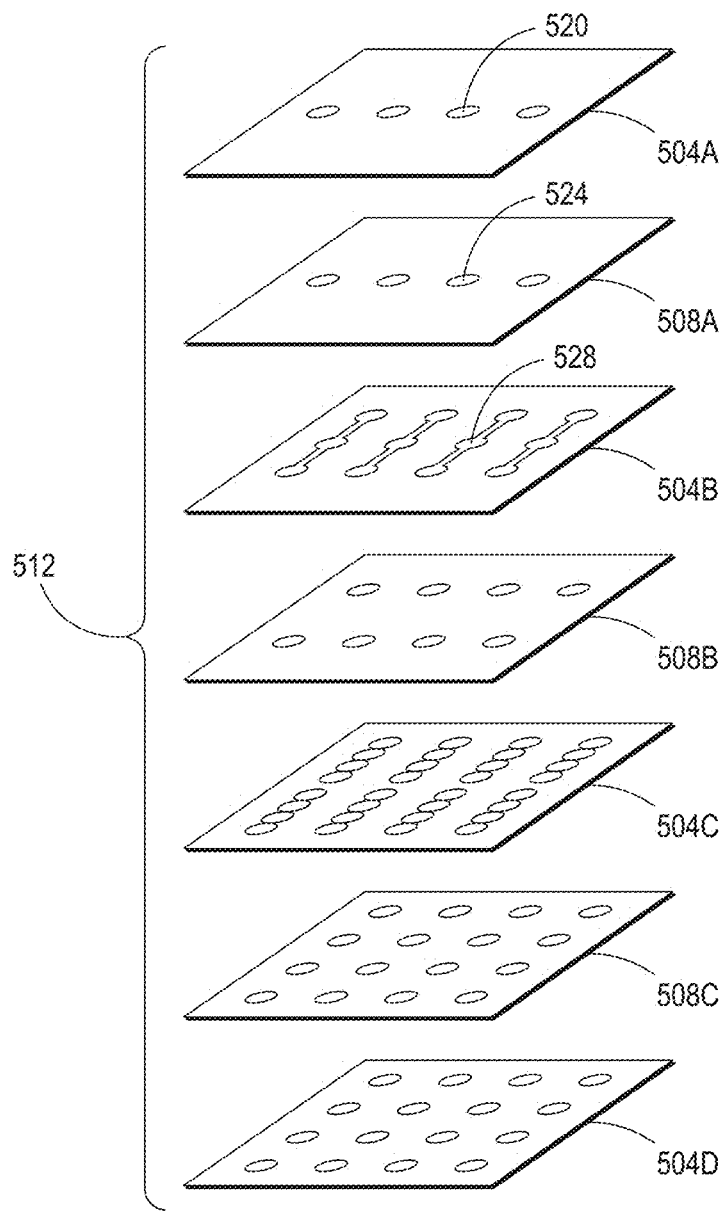
FIG. 6 is a prior art diagram depicting layers of a biomedical testing device that are bonded together with intermediate adhesive layers.

FIG. 5 depicts a series of residual patterns of hydrophobic material that are left on a surface of a first substrate after removal of a second substrate that was bonded to the first substrate. The residual patterns 382, 384, 386, 388, and 390 are formed in a nip at a fixed pressure with the high-temperature first roller 104 having temperatures of 69° C., 79° C., 82° C., 95° C., and 110° C., respectively. In the example of FIG. 5, the nip pressure is approximately 2,500 PSI, although alternative configurations use a pressure range between 800 PSI and 3,000 PSI. As depicted in FIG. 5, the amount of hydrophobic material that penetrates the substrate increases in response to a corresponding increase in the temperature of the first roller. To bond two substrates together, some penetration of the hydrophobic material into both substrates forms the bond. However, if too much hydrophobic material penetrates both substrates, then the bond between the substrates is weakened because there is insufficient hydrophobic material that remains between the two substrates to maintain the bond. In the embodiment of FIG. 5, the pattern 382 that is formed at the lowest temperature of 69° C. shows the greatest degree of residue because a larger portion of the hydrophobic material remains between the two substrates. The level residue is indicative of a stronger bond between the two substrates. As depicted in FIG. 5, the level of residue decreases as the temperature of the first roller increases in the samples 384, 386, 388, and 390.

In addition to bonding substrates together, the hydrophobic material also penetrates the substrate to form fluid channels in some embodiments where the increased temperatures promote the formation of fluid channels where the hydrophobic material completely penetrates the substrate. For example, in FIG. 5 the samples 388 and 390 that are formed with first roller temperatures of 95° C. and 110° C., respectively, depict the phase-change patterns with greater penetration to the first substrate. Consequently, while a temperature near the lower operational range of the first roller in the apparatus forms stronger bonds between substrate layers, the selected first roller temperature is greater in embodiments where the hydrophobic material penetrates the substrates to form fluid channels in addition to bonding the substrates together. As depicted in FIG. 3, the temperature of the first roller is 90° C. in one embodiment that enables the hydrophobic material to penetrate the substrate layers in the biomedical testing device 350 while also forming bonds between the substrate layers that are durable for practical use of the biomedical testing device 350.

It will be appreciated that various of the above-disclosed and other features, and functions, or alternatives thereof, may be desirably combined into many other different systems or applications. Various presently unforeseen or unanticipated alternatives, modifications, variations, or improvements therein may be subsequently made by those skilled in the art, which are also intended to be encompassed by the following claims.

What is claimed is:

1. An apparatus for bonding a first substrate to a second substrate comprising:
    a first roller;
    a second roller configured to engage the first roller to form a nip;
    a first heater operatively connected to the first roller and configured to heat the first roller to a first temperature that is greater than a second temperature of the second roller;
    a substrate transport configured to move the first substrate and a second substrate through the nip simultaneously; and
    a controller operatively connected the first heater and the substrate transport, the controller being configured to:
        activate the first heater to heat the first roller to the first temperature;
        operate the substrate transport to move the first substrate and the second substrate through the nip with a predetermined pattern of a hydrophobic material on the first side of the first substrate engaging a first side of the second substrate, a second side of the first substrate engaging the second roller and a second side of the second substrate engaging the first roller to enable the hydrophobic material in the predetermined pattern to bond the first substrate to the second substrate; and
        operate the first heater to heat the first roller to the first predetermined temperature to produce a temperature gradient in the nip to liquefy the hydrophobic material and enable a first portion of the hydrophobic material to penetrate the first substrate and a second portion of the hydrophobic material to penetrate the second substrate, the first portion being greater than the second portion.

2. The apparatus of claim 1, wherein the temperature gradient in the nip is between approximately 900 C at the first roller and approximately 200 C to 400 C at the second roller.

3. The apparatus of claim 1, wherein the first predetermined temperature of the first roller is between 650 C and 1400 C.

4. The apparatus of claim 1, the hydrophobic material comprising phase-change ink.

5. The apparatus of claim 1, the second roller being configured to engage the first roller with a predetermined pressure to enable the nip to apply pressure to the hydrophobic material in the nip to bond the first substrate to the second substrate.

6. The apparatus of claim 1 further comprising:
    an actuator operatively connected to at least one of the first roller and the second roller; and
    the controller being operatively connected to the actuator and further configured to:
        operate the actuator to rotate the first roller and the second roller at a predetermined velocity that enables a predetermined portion of the first substrate and the second substrate to remain in the nip in a range of approximately 0.1 seconds to 10 seconds.

7. A method of bonding a first substrate to a second substrate comprising:
    activating with a controller a first heater to heat a first roller to the first temperature;

engaging with the controller a second roller to the first roller to form a nip, the second roller having a second temperature that is lower than the first temperature;

operating with the controller a substrate transport to move the first substrate and a second substrate through the nip with a predetermined printed pattern of a hydrophobic material on the first side of the first substrate engaging a first side of the second substrate, a second side of the first substrate engaging the second roller and a second side of the second substrate engaging the first roller to enable the hydrophobic material in the predetermined printed pattern to bond the first substrate to the second substrate; and operating with the controller the first heater to heat the first roller to the first predetermined temperature to produce a temperature gradient in the nip to liquefy the hydrophobic material and enable a first portion of the hydrophobic material to penetrate the first substrate and a second portion of the hydrophobic material to penetrate the second substrate, the first portion being greater than the second portion.

8. The method of claim 7 wherein the temperature gradient in the nip is between approximately 90° C. at the first roller and a range of 20° C. to 40° C. at the second roller.

9. The method of claim 7 wherein the first predetermined temperature of the first roller is between 65° C. and 140° C.

10. The method of claim 7, the hydrophobic material comprising phase-change ink.

11. The method of claim 7, the second roller being configured to engage the first roller with a predetermined pressure to enable the nip to apply pressure to the hydrophobic material in the nip to bond the first substrate to the second substrate.

12. The method of claim 7 further comprising:

operating with the controller an actuator to rotate the first roller and the second roller at a predetermined velocity that enables a predetermined portion of the first substrate and the second substrate to remain in the nip in a range of approximately 0.1 seconds to 10 seconds.

13. A chemical assay device configured to direct a diffusion of a fluid comprising:

a first substrate comprising:

a first side with a predetermined location that is configured to receive a biological fluid sample;

a second substrate with a first side that engages a second side of the first substrate to receive fluid from the biological fluid sample that diffuses through the first substrate; and a hydrophobic material that penetrates the first substrate and the second substrate to bond the first substrate to the second substrate, a first portion of the hydrophobic material penetrates the first substrate and a second portion of the hydrophobic material penetrates the second substrate, the second portion being greater than the first portion.

14. The chemical assay device of claim 13, the first substrate and the second substrate comprising paper.

15. The chemical assay device of claim 14, the hydrophobic material comprising a hydrophobic material that prevents a diffusion of the biological fluid sample through portions of the first substrate and the second substrate that are penetrated by the hydrophobic material.

\* \* \* \* \*